United States Patent
Chung (10) Patent No.: US 9,011,413 B2
(45) Date of Patent: Apr. 21, 2015

(54) ASSEMBLY FOR INSERTING FOLEY CATHETER

(71) Applicant: Kyung Jin Chung, Seoul (KR)

(72) Inventor: Kyung Jin Chung, Seoul (KR)

(*) Notice: Subject to any disclaimer, the term of this patent is extended or adjusted under 35 U.S.C. 154(b) by 13 days.

(21) Appl. No.: 13/747,999

(22) Filed: Jan. 23, 2013

(65) Prior Publication Data

US 2013/0138087 A1 May 30, 2013

Related U.S. Application Data

(63) Continuation of application No. PCT/KR2011/005403, filed on Jul. 22, 2011.

(30) Foreign Application Priority Data

Jul. 23, 2010 (KR) .......................... 10-2010-0071474

(51) Int. Cl.
*A61M 27/00* (2006.01)
*A61M 25/00* (2006.01)
A61M 25/01 (2006.01)

(52) U.S. Cl.
CPC ....... *A61M 25/0017* (2013.01); *A61M 25/0111* (2013.01); *A61M 25/0113* (2013.01)

(58) Field of Classification Search
CPC .......... A61M 25/0017; A61M 25/002; A61M 25/0068; A61M 25/01; A61M 25/0111; A61M 25/0113; A61M 25/013; A61M 25/0133; A61M 25/0136; A61M 2025/01; A61M 2210/1078; A61M 2210/1085; A61M 2210/1089

USPC .......................................... 604/528, 544, 533
See application file for complete search history.

(56) References Cited

U.S. PATENT DOCUMENTS

| | | | | |
|---|---|---|---|---|
| 3,206,782 A | * | 9/1965 | Larsen ....................... 15/104.33 |
| 3,835,854 A | * | 9/1974 | Jewett .............................. 604/159 |
| 6,602,244 B2 | * | 8/2003 | Kavanagh et al. ............. 604/544 |
| 2005/0171568 A1 | * | 8/2005 | Duffy .............................. 606/191 |
| 2008/0319387 A1 | * | 12/2008 | Amisar et al. .............. 604/95.04 |
| 2009/0043287 A1 | * | 2/2009 | Mosler et al. .................. 604/544 |
| 2010/0145315 A1 | * | 6/2010 | House ............................ 604/544 |
| 2010/0174290 A1 | * | 7/2010 | Wuebbeling et al. .......... 606/108 |

* cited by examiner

*Primary Examiner* — Leslie Deak
*Assistant Examiner* — Kai Weng
(74) *Attorney, Agent, or Firm* — Mintz Levin Cohn Ferris Glovsky and Popeo, P.C.; Kongsik Kim (57) ABSTRACT

A Foley catheter assembly is disclosed. The Foley catheter assembly includes a Foley catheter, which includes an insertion tip inserted into the bladder and a drainage tube extending from the insertion tip and draining urine from the bladder, and a catheter support cover, which covers the outer surface of the Foley catheter before insertion of the Foley catheter into the bladder to prevent contamination and allows smooth insertion of the insertion tip into the bladder at a constant speed. The catheter support cover includes a pair of support main bodies that are detachably coupled to each other and accommodate the drainage tube and a pair of transport rollers disposed at both sides of the insertion tip at upper portions of the support main bodies to be rotatable for inserting the insertion tip into the bladder.

5 Claims, 6 Drawing Sheets

ASSEMBLY FOR INSERTING FOLEY CATHETER

CROSS-REFERENCE TO RELATED APPLICATIONS

This application is a continuation of International Application No. PCT/KR2011/005403 filed on Jul. 22, 2011, which claims priority to Korean Application No. 10-2010-0071474 filed on Jul. 23, 2010, which applications are incorporated herein by reference.

BACKGROUND

1. Technical Field

The present invention relates to a Foley catheter assembly, and more particularly, to a Foley catheter assembly for inserting a Foley catheter into the bladder for artificial urination.

2. Related Art

Artificial urination is drainage of urine by inserting a catheter into the bladder through the urethra. A Foley catheter is a urinary catheter for patients who continuously need artificial urination for a predetermined period of time. Artificial urination using a Foley catheter is widely applied to withdraw urine from patients under intensive case, general surgical patients, patients who have undergone urologic surgery, or patients who are otherwise unable to urinate or to measure urine output.

Figure 1:
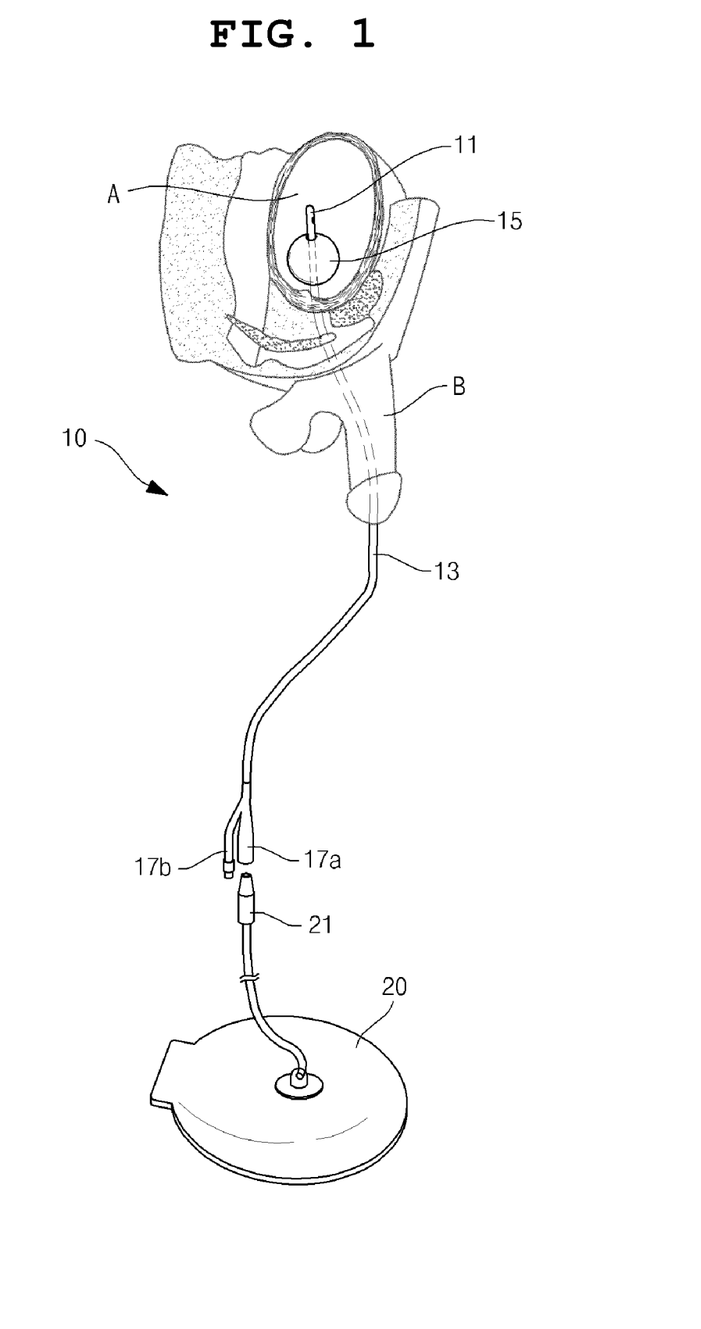
FIG. 1 is a schematic diagram illustrating a state in which a conventional Foley catheter is inserted into the bladder.

FIG. 1 is a schematic diagram illustrating a state in which a Foley catheter 10 is inserted into the bladder for artificial urination. The Foley catheter 10 is a device including an insertion tip 11 and a drainage tube 13, which are inserted into the urethra, for withdrawing urine to a urine collection bag.

However, a process of performing a medical treatment for inserting the Foley catheter 10 into the bladder is troublesome in preparation and treatment stages thereof. A sterile Foley catheter set including drapes, Kelly forceps, and three containers respectively containing lubricating jelly, a saline solution for inflating a balloon, and alcohol swabs needs to be prepared in the hospital. In the preparation, a nurse opens the Foley catheter set, removes a wrapping case from a Foley catheter and a syringe for inflating the balloon, and adds the lubricating jelly, saline solution for inflating a balloon, and alcohol swabs to each of the containers. In order to prevent contamination in each stage, precautions need to be taken. Thus, the preparation is tedious and time-consuming. In terms of hospital management, such preparation of the Foley catheter set and preparation for the treatment may bring about increase in costs and waste of labor of nurses who are highly qualified. Thus, there is a need to develop a device and method of simplifying the preparation process.

Meanwhile, careful treatment is required by a medical professional such as a doctor or nurse to prevent contamination and to insert the catheter into a patient without pain. The prepared Foley catheter set is carefully opened, and the Foley catheter 10 is separated from an inner wrapping case while wearing sterile gloves. The syringe is filled with a saline solution and connected to a saline supply tube 17b to test the balloon 15. Then, a discharge tube 17a is grasped by a Kelly clamp in order not to stain surroundings by preventing leakage of urine during the treatment. An area to be treated is sterilized, a drape is placed over legs of a patient to prevent the Foley catheter 10 from being contaminated during insertion thereof, and then the treatment is performed. In order to smoothly inserting the Foley catheter 10 while minimizing pain, the lubricating jelly is coated over the Foley catheter 10, the urethra is opened with one hand, and the Foley catheter 10 is inserted into the urethra using the other hand. This process is troublesome, time-consuming, and uncomfortable. In addition, although the lubricating jelly needs to be sufficiently and uniformly coated over the Foley catheter 10 to minimize pain, continuous lubrication may cause contamination of portions such as hands or other body parts of the medical professional.

In addition, the patient may feel pain due to friction with mucosa of the urethra while the insertion tip 11 of the Foley catheter 10 is inserted into the urethra of the patient. Thus, the patient may feel serious pain when the medical professional fails to uniformly control insertion speed and insertion force.

SUMMARY

Therefore, the present invention has been made in view of the above problems, and it is an object of the present invention to provide an assembly for inserting a Foley catheter hygienically handled in a sterile condition before insertion of the Foley catheter into a patient even after a wrapping case is removed and simply prepared and processed.

It is another object of the present invention to provide a Foley catheter assembly having improved convenience by uniformly and simply lubricating the entire surface of the Foley catheter with a lubricating jelly by forming a lubricating jelly accommodation space in the Foley catheter assembly, thereby eliminating the need for direct lubrication of an insertion tip with the lubricating jelly by a nurse.

It is a further object of the present invention to provide a Foley catheter assembly capable of relieving pain of a patient by uniformly maintaining insertion speed of the Foley catheter.

In accordance with the present invention, the above and other objects can be accomplished by the provision of a Foley catheter assembly including a Foley catheter including an insertion tip inserted into a bladder and a drainage tube extending from the insertion tip and discharging urine, and a catheter support cover covering the outer surface of the Foley catheter before the Foley catheter is inserted into the bladder for protection from external contamination and assisting the insertion tip to be smoothly inserted into the bladder at a constant speed. The catheter support cover includes a pair of support main bodies having an open slit, detachably coupled to each other, and accommodating the drainage tube, and a pair of transport rollers rotatably disposed in upper portions of the support main bodies at both sides of the insertion tip and transporting the insertion tip into the bladder.

Jelly-containing grooves filled with a lubricating jelly may be formed to a predetermined depth at upper portions of the pair of support main bodies, and the insertion tip and the drainage tube may be continuously lubricated with the lubricating jelly at surfaces thereof while passing through the jelly-containing grooves when the insertion tip is transported by the pair of transport rollers.

The Foley catheter assembly may further include a roller cover disposed at an upper and outer region of the support main bodies and coupled to one of the pair of transport rollers.

The Foley catheter assembly may further include a contamination prevention cap covering the upper portions of the pair of support main bodies and preventing contamination of the insertion tip.

An open slit may be formed on the front surfaces of the pair of support main bodies, and a saline supply tube for supplying a saline solution to the balloon disposed at a lower portion of the insertion tip may protrude through the open slit.

In accordance with an aspect of the present invention, the above and other objects can be accomplished by the provision of a method of inserting a Foley catheter assembly into a bladder including connecting a discharge tube of an externally open connection tube to a urine discharge tube of a urine collection bag, connecting a saline supply tube to a syringe filled with a saline solution in advance outside a catheter support cover, adding a lubricating jelly to jelly-containing grooves of a pair of support main bodies, removing a contamination prevention cap, inserting an insertion tip and a drainage tube into a bladder by rotating a pair of transport rollers, fixing the position of the insertion tip by inflating a balloon by injecting the saline solution into a Foley catheter, and decoupling the pair of support main bodies from each other when the position of the insertion tip is fixed.

Since upper and lower portions of the Foley catheter of the Foley catheter assembly according to the present invention are covered with the catheter support cover and the contamination prevention cap, the Foley catheter may not directly contact external materials, even when a wrapping case is removed, thereby minimizing contamination. Thus, preparation of the Foley catheter set may be more simply and rapidly performed compared to preparation of conventional Foley catheter sets.

In addition, since jelly-containing grooves that accommodate a lubricating jelly are formed in the catheter support cover, the insertion tip and the drainage tube pass through the jelly-containing grooves when they are transported, so that the insertion tip and the drainage tube may be inserted into the urethra in a state that surfaces thereof are uniformly lubricated with the lubricating jelly. Accordingly, there is no need for a medical professional to directly lubricate the Foley catheter with the lubricating jelly, and patient's pain may be reduced.

In addition, since a saline supply tube is located outside of the catheter support cover, it moves as the Foley catheter is inserted, so that the balloon may be inflated from the outside without contamination of the Foley catheter. Thus, the treatment is simply performed.

In addition, since insertion speed of the Foley catheter is uniformly controllable by the medical professional using a pair of transport rollers, patient's pain may be minimized.

In addition, since a pair of support main bodies may be decoupled from each other after insertion of the Foley catheter, a patient wearing the Foley catheter may move more freely.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Hereinafter, a preferred embodiment of the present invention will be described with reference to the accompanying drawings for sufficient understanding of the present invention. Various other modified embodiments of the present invention may be provided and the scope of the present invention should not be limited to the embodiment that will be described hereinafter in detail. The embodiment of the present invention is given to more completely explain the present invention to those skilled in the art. Accordingly, it will be appreciated that, in the drawings, dimensions of elements may be exaggerated for clarity, and the same elements are denoted by the same reference numerals even though they are depicted in different drawings. In the following description of the present invention, a detailed description of known functions and configurations incorporated herein will be omitted when it may make the subject matter of the present invention rather unclear.

Figure 2:
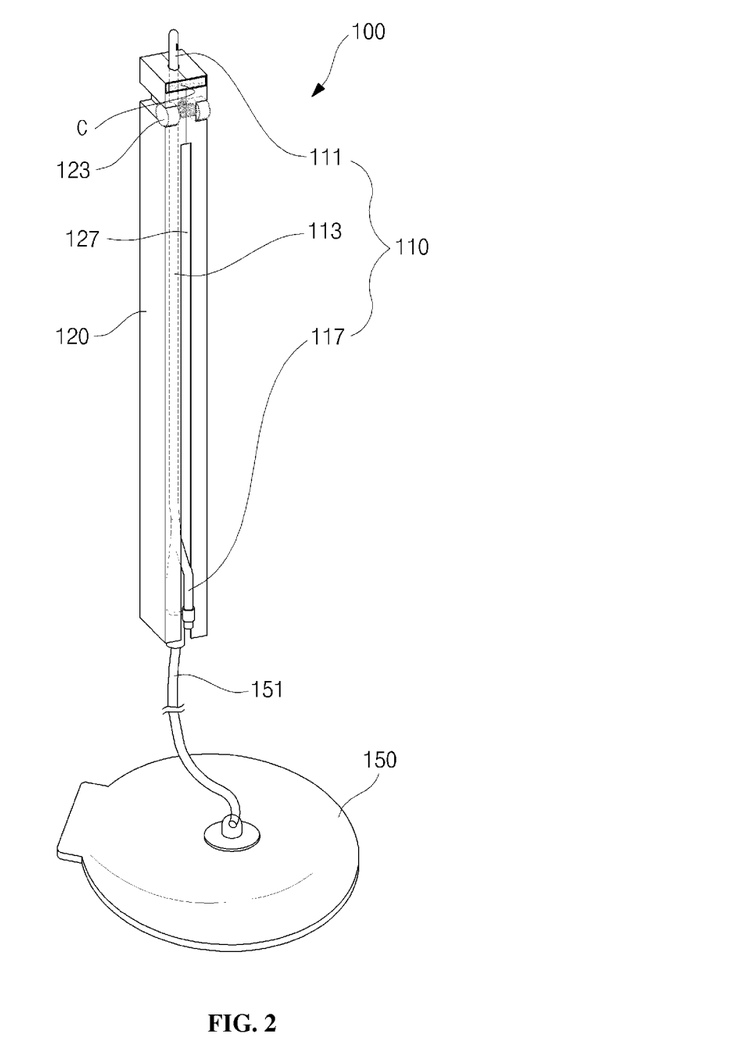
FIGS. 2 and 3 are perspective views illustrating the configuration of a Foley catheter assembly according to the present invention.
Figure 3:
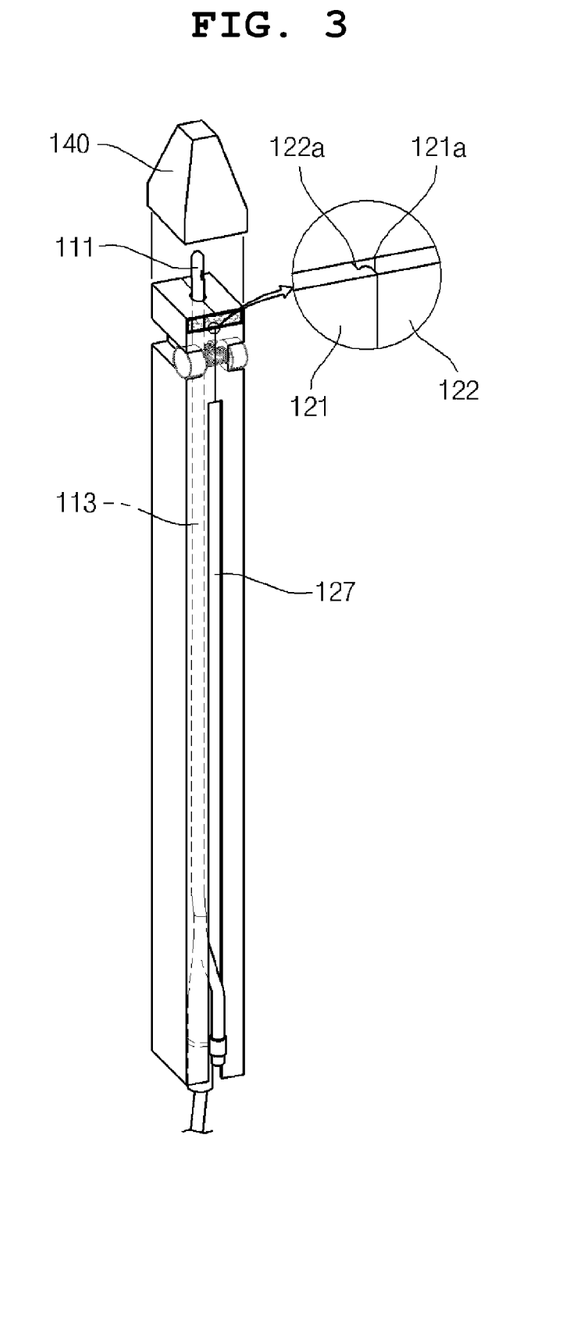
Figure 4:
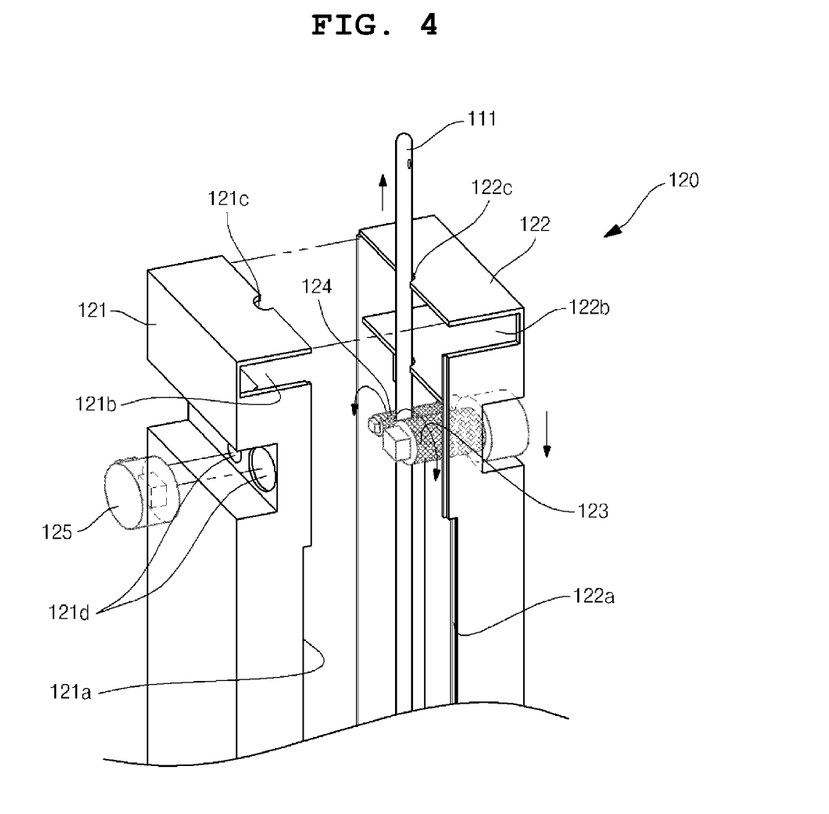
FIG. 4 is an exploded perspective view illustrating the configuration of an upper portion of a Foley catheter assembly according to the present invention.
Figure 5:
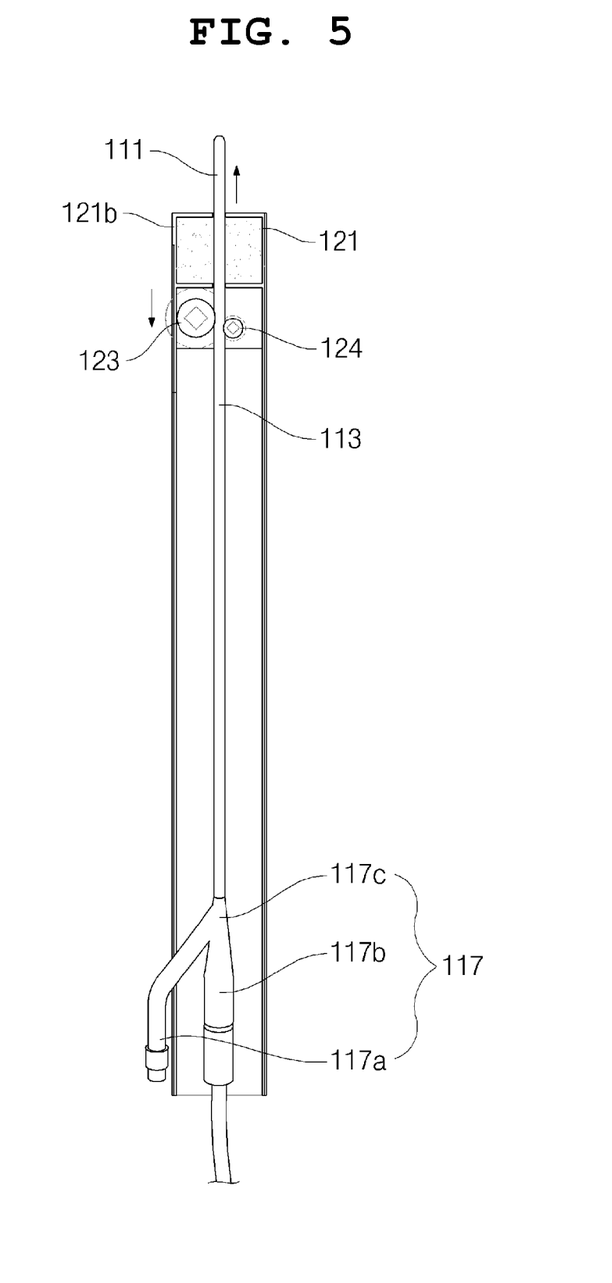
FIG. 5 is a cross-sectional view illustrating a Foley catheter assembly according to the present invention.
Figure 6:
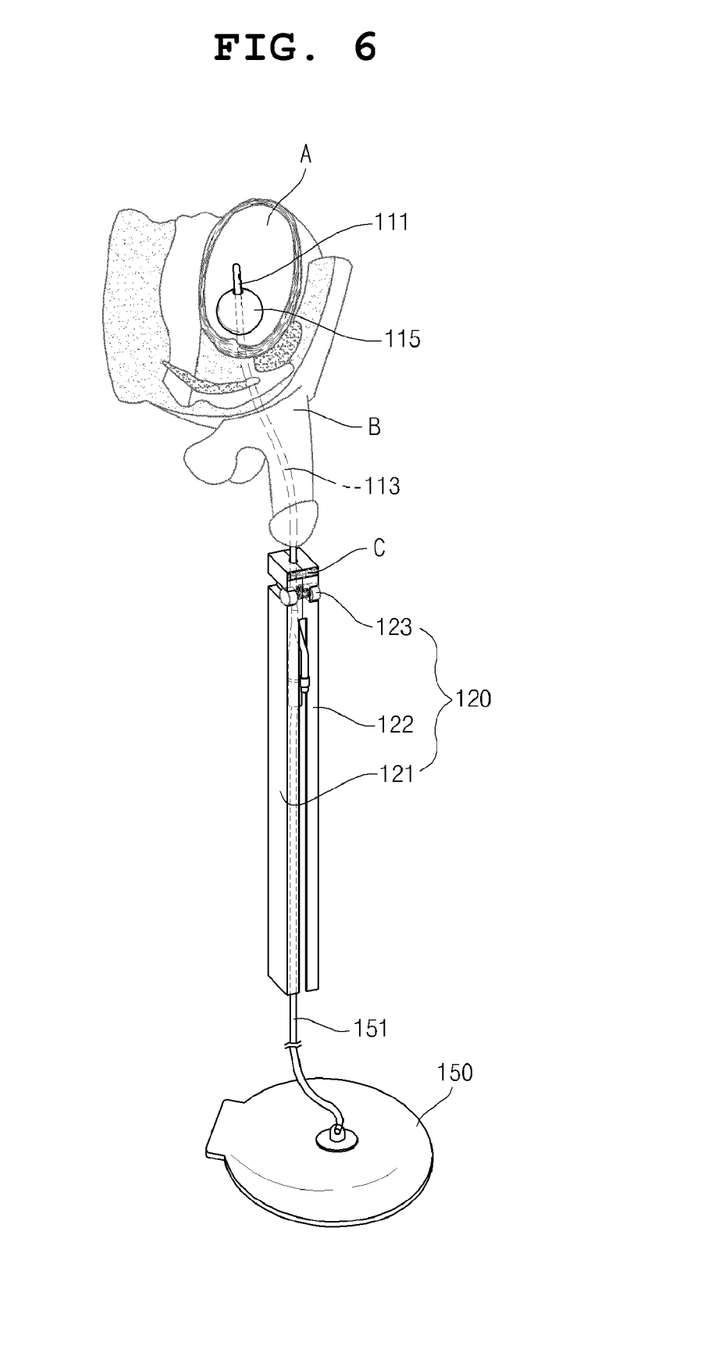
FIG. 6 is a schematic diagram illustrating a state in which a Foley catheter assembly according to the present invention is inserted into the bladder.

FIGS. 2 and 3 are perspective views illustrating the configuration of a Foley catheter assembly 100 according to the present invention. FIG. 4 is an exploded perspective view illustrating the configuration of an upper portion of the Foley catheter assembly 100. FIG. 5 is a cross-sectional view illustrating the Foley catheter assembly 100. FIG. 6 is a schematic diagram illustrating a state in which the Foley catheter assembly 100 is inserted into a bladder.

In this regard, in the drawings, the Foley catheter assembly 100 inserted into a male patient is illustrated. However, the Foley catheter assembly 100 according to the present invention may also be used for female patients in the same manner.

A Foley catheter 110 is inserted into the bladder A to artificially drain urine from the body. The Foley catheter 110 includes an insertion tip 111 inserted into the bladder A, a drainage tube 113 extending from the insertion tip 111 and discharging urine into a urine collection bag 150, a balloon 115 fixing the position of the insertion tip 111, and a branch tube 117 branched from the drainage tube 113.

The branch tube 117 includes a saline supply tube 117*a* for supplying a saline solution to inflate the balloon 115, a discharge tube 117*b* draining urine into the urine collection bag 150, and a connection tube 117*c* connected to the drainage tube 113. The saline supply tube 117*a* protrudes from the catheter support cover 120 through an open slit 127. Accordingly, the balloon 115 may be inflated by supplying a saline solution via the saline supply tube 117*a* from the outside without contaminating the discharge tube 117*b*.

The other elements of the Foley catheter 110 are identical to those of conventional Foley catheters, and thus a detailed description thereof will not be provided herein.

The catheter support cover 120 covers the outer surface of the Foley catheter 110 to prevent contamination of the Foley catheter 110 before insertion into the urethra B of a patient. The catheter support cover 120 has an open slit 127 and includes a pair of support main bodies 121 and 122, which are detachably coupled to each other, and a pair of transport rollers 123 and 124, which are disposed at upper portions of the support main bodies 121 and 122 and transport the insertion tip 111 and the drainage tube 113 into the urethra B.

The support main bodies 121 and 122 are detachably coupled to each other and accommodate the insertion tip 111 and the drainage tube 113 as illustrated in FIG. 4. The support main bodies 121 and 122 respectively have a length corresponding to that of the drainage tube 113 and are formed of a hard material in order to protect the Foley catheter 110 from external contaminants and facilitate insertion of the Foley catheter 110 by maintaining the open slit 127. Accordingly, there is no need to place a drape to prevent contamination during insertion of the Foley catheter 110.

As illustrated in FIG. 3, the support main bodies 121 and 122 have coupling grooves 121*a* and 122*a* corresponding to each other such that outer surfaces of the support main bodies 121 and 122 may be engaged to each other. Thus, the support main bodies 121 and 122 may be easily coupled or decoupled by external force applied thereto.

In addition, the support main bodies 121 and 122 respectively have jelly-containing grooves 121b and 122b that are formed to a predetermined depth at upper portions of the support main bodies 121 and 122. Since the jelly-containing grooves 121b and 122b are disposed at upper portions of the support main bodies 121 and 122, the insertion tip 111 and the drainage tube 113 pass therethrough during insertion into the bladder A.

The jelly-containing grooves 121b and 122b are filled with a lubricating jelly C by a medical professional, and thus the insertion tip 111 and the drainage tube 113, surfaces of which are coated with the lubricating jelly C, are inserted into the urethra B. Thus, the lubricating jelly C may be uniformly coated on the surfaces of the insertion tip 111 and the drainage tube 113 without performing conventional troublesome processes, for example, preparation of a lubricating jelly container in the Foley catheter set, adding the lubricating jelly C to the Foley catheter set, and directly coating the lubricating jelly C on the surfaces of the insertion tip 111 and the drainage tube 113.

Tube accommodation grooves 121c and 122c, which support the insertion tip 111 and the drainage tube 113 and secure the positions thereof, are formed at the center of the support main bodies 121 and 122. The tube accommodation grooves 121c and 122c are formed to correspond to diameters of the insertion tip 111 and the drainage tube 113 to prevent the insertion tip 111 from moving.

Roller accommodation holes 121d where the transport rollers 123 and 124, namely, first and second transport rollers 123 and 124, are disposed are provided below the jelly-containing grooves 121b and 122b. The transport rollers 123 and 124 are disposed in the roller accommodation holes 121d. The transport rollers 123 and 124 are respectively disposed at both sides of the drainage tube 113 to be rotatable in opposite directions to transport the Foley catheter 110 as shown in FIG. 4. Accordingly, when a medical professional rotates the first transport roller 123 rotates by rolling a roller cover 125 using fingers, the Foley catheter 110 moves in response to the rotation of the first transport roller 123, followed by the second transport roller 124 rotating. As a result, the drainage tube 113 disposed at nip regions of the transport rollers 123 and 124 is inserted into the urethra B by rotation of the transport rollers 123 and 124.

In this regard, since the rotation speed of the first transport roller 123 by the medical professional is kept constant, the speed of inserting the insertion tip 111 and the drainage tube 113 into the urethra B may also be kept constant. Thus, patient's pain may be minimized.

The roller cover 125 that fixes the position of the first transport roller 123 is provided to the roller accommodation holes 121d of the support main bodies 121 and 122.

The catheter support cover 120 is provided with a contamination prevention cap 140 at an upper portion of the catheter support cover 120 as illustrated in FIG. 3. The contamination prevention cap 140 is formed of a transparent material such that the balloon 15 may be tested and visually examined by slightly moving the Foley catheter 110 forward. The contamination prevention cap 140 covers an upper portion of the catheter support cover 120 when a wrapping case (not shown) is removed to prevent the insertion tip 111 from contacting external materials. The contamination prevention cap 140 is removed immediately before the Foley catheter 110 is inserted.

Accordingly, the upper portion of the Foley catheter 110 is protected by the contamination prevention cap 140, and the drainage tube 113 and a lower portion of the insertion tip 111 are protected from external contamination by the support main bodies 121 and 122. Thus, the medical professional does not need to perform additional treatment to prevent contamination of the Foley catheter 110 after the wrapping case (not shown) is removed and before the Foley catheter 110 is inserted into the urethra B of the patient. As a result, the medical professional may simply and rapidly perform the procedure.

In addition, since the Foley catheter 110 is protected by the catheter support cover 120 even after the wrapping case (not shown) is removed, the open discharge tube 117b of the branch tube 117 may be connected to the urine discharge tube 151 of the urine collection bag 150 without performing a further aseptic treatment. Thus, a Kelly clamp for inhibiting leakage of urine in the Foley catheter set is not required, and subsequent procedures may be simply performed.

Then, the saline supply tube 117a is connected to a syringe (not shown) filled with a saline solution at the outside of the catheter support cover 120, and the Foley catheter 110 is inserted thereinto, so that the balloon 115 may be simply inflated. Thus, a conventional process of preparing a container for a saline solution used to inflate the balloon 115 in the Foley catheter set and adding the saline solution to the container of the Foley catheter set during preparation for inserting the Foley catheter 110 is not required.

Thus, conventional Foley catheter sets, complicated insertion preparation processes, and sterile gloves are not required, and the lubricating jelly and the syringe filled with a saline solution may be simply prepared during the treatment. Thus, preparation for inserting the Foley catheter may be completed by preparing a general dressing set including alcohol swabs.

A process of inserting the Foley catheter assembly 100 according to the present invention having the configuration as described above will be described with reference to FIGS. 2 to 6.

First, the wrapping case (not shown) accommodating the Foley catheter assembly 100 is removed by the medical professional to expose the Foley catheter assembly 100. Here, careful handling of the open discharge tube 117b is required to prevent contamination.

In addition, the open discharge tube 117b of the branch tube 117 is connected to the urine discharge tube 151 of the urine collection bag 150, and the saline supply tube 117a is connected to the syringe (not shown) filled with a saline solution (air). Then, the Foley catheter 110 is slightly moved forward using the transport roller 123 to locate the balloon 115 in the contamination prevention cap 140. The Foley catheter 110 is tested by inflating the balloon 115, followed by locating the Foley catheter 110 at the original position. In addition, as illustrated in FIG. 2, the lubricating jelly C is added to the catheter support cover 120 of the exposed Foley catheter assembly 100.

When the Foley catheter assembly 100 is ready to use, the urethra B is sterilized using an alcohol swab, the entrance of urethra is secured by one hand of the medical professional, the contamination prevention cap 140 is removed by the other hand of the medical professional, the insertion tip 111 is located at the urethra B, and the first transport roller 123 is rotated. As illustrated in FIG. 5, the drainage tube 113 disposed between the transport rollers 123 and 124 moves upward along with the rotation of the transport rollers 123 and 124, and the insertion tip 111 is transported to the bladder A through the urethra B.

In this regard, the insertion tip 111 may be inserted at a constant speed by the medical professional by smoothly rotating the transport rollers 123 and 124 at a constant speed.

Meanwhile, since the insertion tip 111 and the drainage tube 113 transported into the urethra B pass through the jelly-containing grooves 121b and 122b, the lubricating jelly C is continuously and uniformly coated on the surfaces thereof while moving. Thus, the Foley catheter 110 may be smoothly inserted into the urethra B, so that patient's pain is prevented.

The location of the insertion tip 111 may be confirmed by the medical professional using the location of the branch tube 117. When the insertion tip 111 is located in the bladder A, a predetermined amount of the saline solution (air) is injected through the syringe (not shown) connected thereto in advance to inflate the balloon 115. As the balloon 115 is inflated, the insertion tip 111 is fixed in the bladder A.

Drainage of urine is tested to determine whether the Foley catheter 110 is properly inserted. When the insertion of the Foley catheter 110 is completed, the support main bodies 121 and 122 are decoupled from each other to allow the patient wearing the Foley catheter 110 to move more freely.

As apparent from the above description, since upper and lower portions of the Foley catheter of the Foley catheter assembly according to the present invention are covered with the catheter support cover and the contamination prevention cap, the Foley catheter may not be directly exposed to external air, even when the wrapping case is removed, thereby minimizing contamination.

Thus, the medical professional may simply and rapidly perform the treatment.

In addition, since the insertion speed of the Foley catheter may be uniformly controlled by the medical professional using a pair of transport rollers, patient's pain is minimized.

In addition, since the support main bodies may be separated from the Foley catheter after insertion of the Foley catheter, the patient may move more freely.

Although the preferred embodiment of the Foley catheter assembly according to the present invention has been disclosed for illustrative purposes, those skilled in the art will appreciate that various modifications, additions and substitutions are possible. Thus, it will be easily understood that the present invention is not limited to the above mentioned configuration. Accordingly, the scope of the present invention should not be limited to the description of the embodiment, but defined by the accompanying claims and equivalents thereof.

What is claimed is:

1. A Foley catheter assembly comprising:
a Foley catheter comprising an insertion tip configured to be inserted into a bladder and a drainage tube extending from the insertion tip and configured to discharge urine; and
a detachable catheter support cover covering an outer surface of the Foley catheter before the Foley catheter is inserted into the bladder for protection from external contamination and assisting the insertion tip to be smoothly inserted into the bladder at a constant speed and removable once the insertion tip is smoothly inserted into the bladder;
wherein the catheter support cover comprises:
a pair of support main bodies having an open slit, detachably coupled to each other, and accommodating the drainage tube; and
a pair of transport rollers rotatably disposed to transport the insertion tip into the bladder in upper portions of the support main bodies at both sides of the insertion tip,
wherein the open slits is formed on front surfaces of the pair of support main bodies, and
wherein the drainage tube is connected to a branch tube including a saline supply tube, a discharge tube, and a connection tube such that the saline supply tube protrudes out of the catheter support cover through the open slit while the discharge tube and the connection tube are covered by the catheter support cover.

2. The Foley catheter assembly according to claim 1, wherein jelly-containing grooves filled with a lubricating jelly are formed to a predetermined depth at upper portions of the pair of support main bodies, and the insertion tip and the drainage tube are continuously lubricated with the lubricating jelly at surfaces thereof while passing through the jelly-containing grooves when the insertion tip is transported by the pair of transport rollers.

3. The Foley catheter assembly according to claim 1, further comprising a roller cover disposed at an upper and outer region of the support main bodies and coupled to one of the pair of transport rollers 4. The Foley catheter assembly according to claim 2, further comprising a contamination prevention cap covering the upper portions of the pair of support main bodies and preventing contamination of the insertion tip.

5. A method of inserting a Foley catheter assembly into a bladder, the method comprising:
connecting a discharge tube of an externally open connection tube to a urine discharge tube of a urine collection bag;
connecting a saline supply tube to a syringe filled with a saline solution in advance outside a catheter support cover;
adding a lubricating jelly to jelly-containing grooves of a pair of support main bodies; removing a contamination prevention cap;
inserting an insertion tip and a drainage tube into a bladder by rotating a pair of transport rollers;
fixing the position of the insertion tip by inflating a balloon by injecting the saline solution into a Foley catheter; and
decoupling the pair of support main bodies from each other and the catheter when the position of the insertion tip is fixed.

* * * * *